March 20, 1951 P. J. HOWARD Plant Pat. 1,009
ROSE PLANT
Filed Nov. 4, 1949
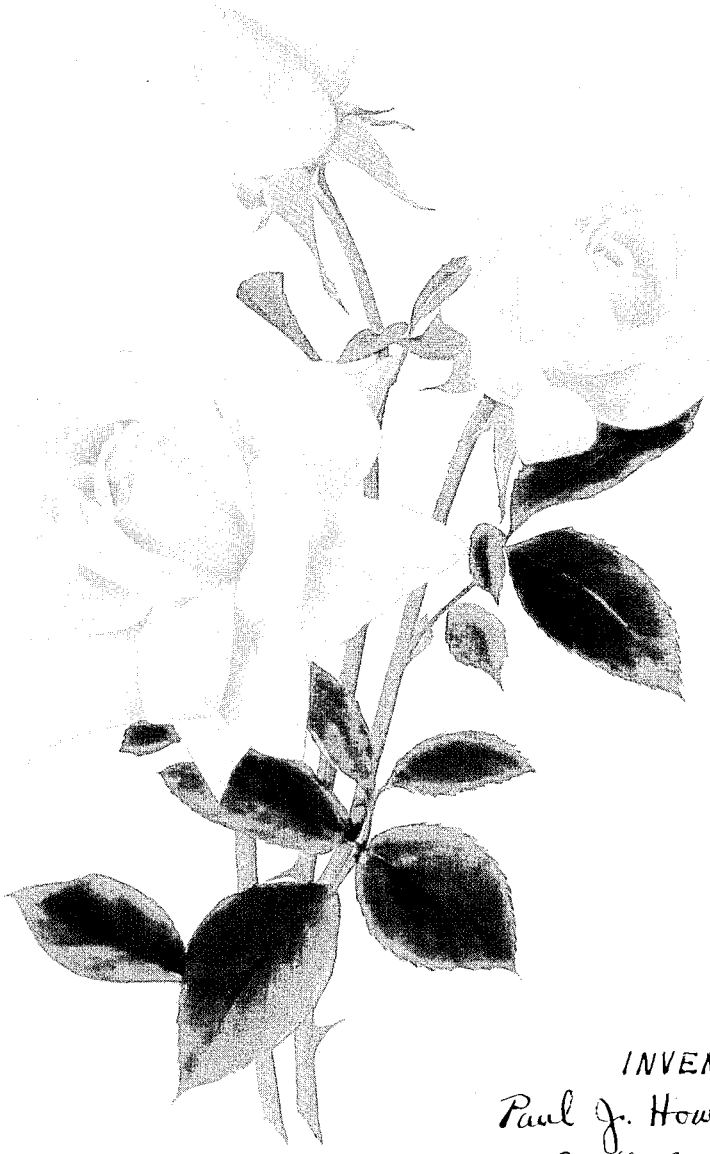
INVENTOR
Paul J. Howard
By Orville M. Kile
Plant Pat Agent Patented Mar. 20, 1951

Plant Pat. 1,009

UNITED STATES PATENT OFFICE 1,009

ROSE PLANT

Paul J. Howard, Los Angeles, Calif., assignor to Paul J. Howard California Flowerland, Los Angeles, Calif., a corporation Application November 4, 1949, Serial No. 125,433

1 Claim. (Cl. 47—61)

My present invention relates to a new variety of hybrid tea rose plant originating as the result of a cross between the varieties Los Angeles (not patented) and California (Plant Patent No. 449). The cross was made by me in my gardens in Los Angeles and the new variety has been asexually reproduced by means of budding at the same locality—the characteristic features appearing to be permanent.

The new variety is a very vigorous and healthy grower and is free in its production of very large flowers of heavy substance. Outstanding among its features is its abundant rich leathery foliage which grows close to the flower, the slow opening of its bud, and the fragrance and good form of its flower.

Illustrations accompanying these specifications show in approximately true colors, three specimens of the bloom of this variety in various stages of opening.

Following is a detailed description of this new variety of rose in which color plate numbers refer to Ridgway's Color Standards and Nomenclature.

*The plant*

Growth: Vigorous, upright bush, normally growing 3 to 3½ feet high. As a rule each branch produces just a single flower at the terminal of the stem, thus making long flower stems.

Blooming habit: Continuous.

Stems.—Heavy; straight; very strong and stiff. Color dark green tinged with red. Thorns moderate in number; sharp; red-tinged; extending at right angles.

Foliage:

*Quantity.*—Abundant and luxuriant.

*Leaflets.*—Three to five.

*Size.*—Medium to large, terminal leaflets approximately 2½ inches long by 1½ inches wide.

*Shape.*—Elliptical with acuminate apex. Edge finely serrated.

*Aspect.*—Glossy.

*Texture.*—Leathery.

*Health.*—Resistant to most rose diseases.

*Color.*—Rich green, approximately Elm Green (Pl. XVII).

*Rachis.*—Medium size. Grooved above. A few small thorns appear on under side. Very short below first leaflet, making leaflet almost sessile.

*Stipules.*—Short and clinging.

*The flower*

Bud:

*Shape.*—Long ovoid.

*Size.*—Large—about 2¼ inches long just before expanding.

*Color.*—Closed bud just showing color is approximately Light Coral Red (Pl. XIII). When first petals begin to open, the inner surface is approximately Apricot Yellow (Pl. IV).

*Opening.*—Extremely slow. Not affected by adverse weather conditions.

*Peduncle.*—Short, strong and heavy. Capable of holding the heavy flowers upright. Usually red-tinged and bearing a number of spines near the bud or flower.

*Sepals.*—Broad; slightly foliaceous; reflex early but do not clasp stem.

Bloom:

*Borne.*—Singly, usually at terminal of long stem.

*Size.*—Medium to large. Sometimes attains a size of six inches in diameter in most favorable conditions, but averages about 4 inches.

*Form.*—Globular with very high center, this form being retained and the flower seldom opening to reveal the stamens.

*Petalage.*—Double, with 35 to 45 petals.

*Color.*—Approximately Apricot Yellow (Pl. IV).

*Fragrance.*—Moderate to intense.

*Longevity.*—Because of the slow opening, the flowers last exceedingly well on the bush, and they also last well as cut flowers.

*Behavior.*—Petals drop freely at maturity.

Petals:

*Shape.*—Almost round. In the open state some of the outer petals reflex in a pointed effect.

*Aspect.*—Silky.

*Texture.*—Very heavy.

*Size.*—Large, being 2½ inches or more in each direction (outer petals).

*Color.*—Basic color of the open flower lies between Light Orange Yellow (Pl. III) and Apricot Yellow (Pl. IV), with shadings of Apricot Buff (Pl. XIV) to Apricot Orange (Plate XIV) on the outer surface of the petals. Although the petals are a little darker on the outer surface due to the shadings, the rose is not a true bicolor rose.

Reproductive organs:

*Anthers.*—Brilliant light red. *Stigmas* yellow. *Pollen* yellow.

*Calyx.*—Small, about 1½ inches by ½ inch.

*Comparison*

The variety most like my new variety is one of its parents, California (Plant Patent No. 449). The principal differences are as follows:

1. The flower of my variety has more petals.
2. The petals of my variety are of firmer substance.
3. The flower of my variety is more fragrant.
4. The color of the two flowers is different—California being a true bi-color and my variety having a flower lighter in color than one of the colors of California.
5. The flowers of my variety are two or three times slower in opening.
6. The general foliage effect of my variety is more luxuriant, more abundant and more disease resistant and the leaflets are usually a little larger.

7. Usually my variety produces just one flower at the terminal of a long branch, while California breaks freely along the flowering stems.
8. My variety produces flowers that are much longer-lasting, particularly on the bush.

Having thus disclosed my invention, I claim:

The new and distinct variety of hybrid tea rose plant, substantially as herein shown and described, characterized particularly by its healthy, abundant foliage which is rich green, glossy and leathery; its habit of producing flowers only at terminals of the branches; and the very large, slow-opening and long-lasting flowers of firm substance, high-centered and lasting form, moderate fragrance and general orange-apricot color.

PAUL J. HOWARD.

No references cited.